(12) United States Patent
Fujiwara

(10) Patent No.: US 10,473,321 B2
(45) Date of Patent: Nov. 12, 2019

(54) TREATMENT LUMINAIRE AND MIRROR APPARATUS

(71) Applicant: Panasonic Intellectual Property Management Co., Ltd., Osaka (JP)

(72) Inventor: Yuri Fujiwara, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 50 days.

(21) Appl. No.: 15/903,870

(22) Filed: Feb. 23, 2018

(65) Prior Publication Data

US 2018/0245786 A1    Aug. 30, 2018

(30) Foreign Application Priority Data

Feb. 27, 2017    (JP) ................. 2017-034912

(51) Int. Cl.
| | |
|---|---|
| *F21V 33/00* | (2006.01) |
| *A47B 67/00* | (2006.01) |
| *F21V 23/04* | (2006.01) |
| *H05B 33/08* | (2006.01) |
| *F21W 131/302* | (2006.01) |

(52) U.S. Cl.
CPC .......... *F21V 33/004* (2013.01); *A47B 67/005* (2013.01); *F21V 23/0492* (2013.01); *F21V 33/0012* (2013.01); *H05B 33/0845* (2013.01); *F21W 2131/302* (2013.01)

(58) Field of Classification Search
CPC .............. F21V 33/004; F21V 23/0492; F21V 33/0012; A47B 67/005; A61N 5/0618; A61N 2005/0642; A61N 2005/0662; A61N 2005/0665; H05B 33/0845; H05B 37/0227; F21W 2131/302
See application file for complete search history.

(56) References Cited

U.S. PATENT DOCUMENTS

| | | | |
|---|---|---|---|
| 2015/0159856 A1* | 6/2015 | Adachi | ................... A47G 1/02 362/141 |
| 2017/0259080 A1 | 9/2017 | Fujiwara | |

FOREIGN PATENT DOCUMENTS

| | | |
|---|---|---|
| JP | 03-297004 A | 12/1991 |
| JP | 04-122209 A | 4/1992 |
| JP | 04-129195 A | 4/1992 |
| JP | 05-174977 A | 7/1993 |
| JP | 11-39916 A | 2/1999 |
| JP | 2009-028254 A | 2/2009 |
| JP | 2009-272094 A | 11/2009 |
| JP | 2013-255687 A | 12/2013 |
| JP | 2013-255688 A | 12/2013 |
| JP | 2013-255689 A | 12/2013 |
| JP | 2014-157428 A | 8/2014 |
| JP | 2017-163359 A | 9/2017 |

\* cited by examiner

*Primary Examiner* — Bao Q Truong
(74) *Attorney, Agent, or Firm* — McDermott Will & Emery LLP

(57) ABSTRACT

A treatment luminaire includes: a first light source; a second light source; a hinge for adjusting a crossing angle between the light distribution axis of the first light source and the light distribution axis of the second light source; and a controller which switches, according to the crossing angle, operation modes of the first light source and the second light source between a normal mode for emitting illumination light for illuminating a surrounding area and a treatment mode for emitting treatment light for therapeutic use.

20 Claims, 6 Drawing Sheets

LIGHT DISTRIBUTION AXIS

TREATMENT LUMINAIRE AND MIRROR APPARATUS

CROSS REFERENCE TO RELATED APPLICATION

This application claims the benefit of priority of Japanese Patent Application Number 2017-034912 filed on Feb. 27, 2017, the entire content of which is hereby incorporated by reference.

BACKGROUND

1. Technical Field

The present disclosure relates to a treatment luminaire which emits light having therapeutic effects and a mirror apparatus provided with the treatment luminaire.

2. Description of the Related Art

Washstands with lights for emitting light forward have conventionally been known (for example, see Japanese Unexamined Patent Application Publication No. 5-174977).

SUMMARY

Such conventional washstands emit light forward, and users are dazzled by the light. For this reason, there is a problem that the users have difficulty in visually checking makeup etc.

In view of this, the present disclosure has an object to provide a treatment luminaire and a mirror apparatus which emit light in such a manner that users are less dazzled by the incident light.

In order to achieve the above object, a treatment luminaire according to an aspect of the present disclosure includes: a first light source; a second light source; an adjuster for adjusting a crossing angle between a light distribution axis of the first light source and a light distribution axis of the second light source; and a controller which switches, according to the crossing angle, operation modes of the first light source and the second light source between a normal mode for emitting illumination light for illuminating a surrounding area and a treatment mode for emitting treatment light for therapeutic use.

In order to achieve the above object, a mirror apparatus according to an aspect of the present disclosure includes: the treatment luminaire; a first mirror on which the first light source is disposed; and two second mirrors arranged on different sides of the first mirror, wherein two second light sources are each disposed on a corresponding one of the second mirrors.

According to the present disclosure, the users are less dazzled by the incident light.

BRIEF DESCRIPTION OF DRAWINGS

The figures depict one or more implementations in accordance with the present teaching, by way of examples only, not by way of limitations. In the figures, like reference numerals refer to the same or similar elements.

DETAILED DESCRIPTION OF THE EMBODIMENT

Figure 1:
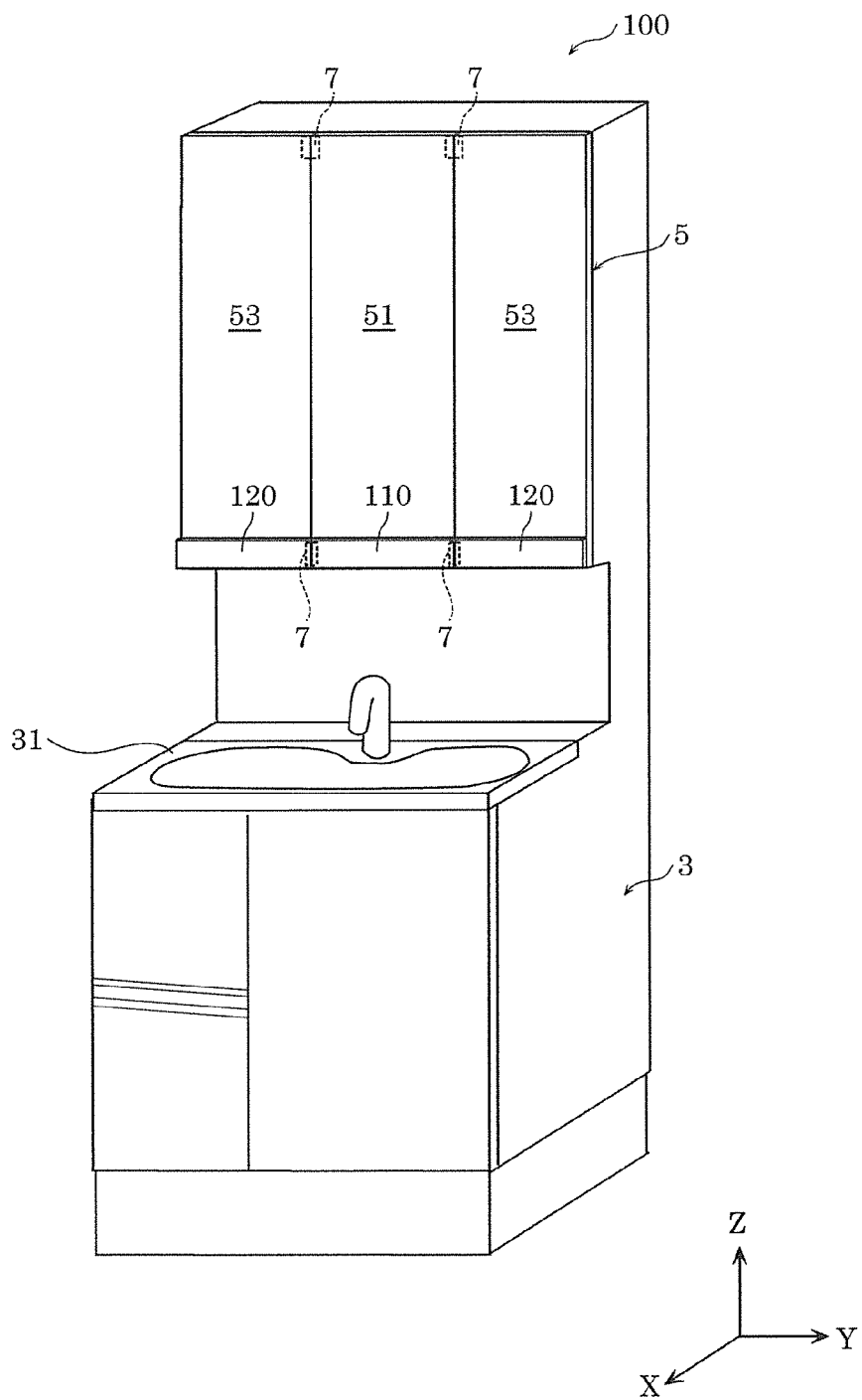
FIG. 1 is a schematic view of a mirror apparatus according to an embodiment.

Underlying Knowledge Forming Basis of the Present Disclosure

In recent years, light therapy has been applied to people suffering seasonal depression, delayed sleep-phase syndrome, circadian rhythm disorder because of premenstrual syndrome, sleepiness, insomnia, etc. Through the application of light having a high illuminance from morning to around 15 o'clock, it is possible to adjust melatonin secretion rhythms and circadian rhythms (biorhythms), thereby mitigating these symptoms. A biorhythm is a rhythm in which a person naturally gets sleepy at a certain time of day and naturally wakes up after certain hours of sleep, occurring as a human physiological phenomenon in a cycle of about one day.

It has been generally known that light having a predetermined wavelength when applied to the eyes of people adjusts their biorhythms. Such light which adjusts their biorhythms includes, for example, blue light. It has been known that blue light provides an effect of improving the biorhythms of people when the people receive light containing blue light during daytime. It has been particularly known that, a predetermined amount or more of blue light when being applied to a person during daytime provides effects of increasing the amount of secretion of melatonin which is living hormone, advancing the phase in change of the amount of secretion in one day. For this reason, it is desirable that such blue light is applied to the eyes of the person to improve his or her biorhythm.

Light when received by a person facilitates generation of melatonin related to his or her biorhythm (biological clock), and thus the person can have a good sleep.

It has been generally known that light having a peak wavelength of around 480 nm accelerates melatonin secretion most due to the sensitivity of human eyes. For this reason, it is desirable that light applied to human eyes include light having a peak wavelength of around 480 nm.

In view of this, humans need to receive light efficiently through their eyes. When light having a high luminance enters the eyes of a person, however, the light causes a physiological phenomenon that his or her pupils contract and the person naturally screws up his or her eyes. In other words, the person is dazzled by the high-luminance light. For this reason, it is difficult to perform an appropriate visual check only by receiving such light from a conventional apparatus.

In order to reduce such glare, it is conceivable to provide a diffuser panel or the like on the light emission side of a light source. Such a diffuser panel, however, inevitably increases the size of a treatment luminaire and the manufacturing cost.

For this reason, there is a demand for causing blue light to enter the eyes of people without causing the people to be dazzled by the light. For this reason, the present disclosure provides a treatment luminaire and a mirror apparatus which emit light in such a manner that people are less dazzled by the incident light.

Hereinafter, the embodiment of the present disclosure is described with reference to the drawings. The embodiment described below illustrates one example of the present disclosure. Thus, the numerical values, shapes, materials, constituent elements, the arrangement and connection of the constituent elements described in the following embodiment are merely examples and not intended to limit the present disclosure. Accordingly, among the constituent elements in the following embodiment, the constituent elements that are not recited in any independent claim that defines the most generic concept of the present disclosure are described as arbitrary constituent elements.

In addition, the phrase "approximately . . . " is used, in an exemplary case of "approximately the same one", to include not only "the same one" but also "substantially the same one". The phrase "near . . . " is used in the same meaning.

Incidentally, each of the diagrams is a schematic view and not necessarily illustrated in a strict manner. Furthermore, in each of the diagrams, substantially the same elements are assigned the same reference signs, and the redundant descriptions of such elements are omitted or simplified.

Embodiment

Hereinafter, a treatment luminaire and a mirror apparatus according to an embodiment of the present disclosure are described.

[Configuration]

Figure 2:
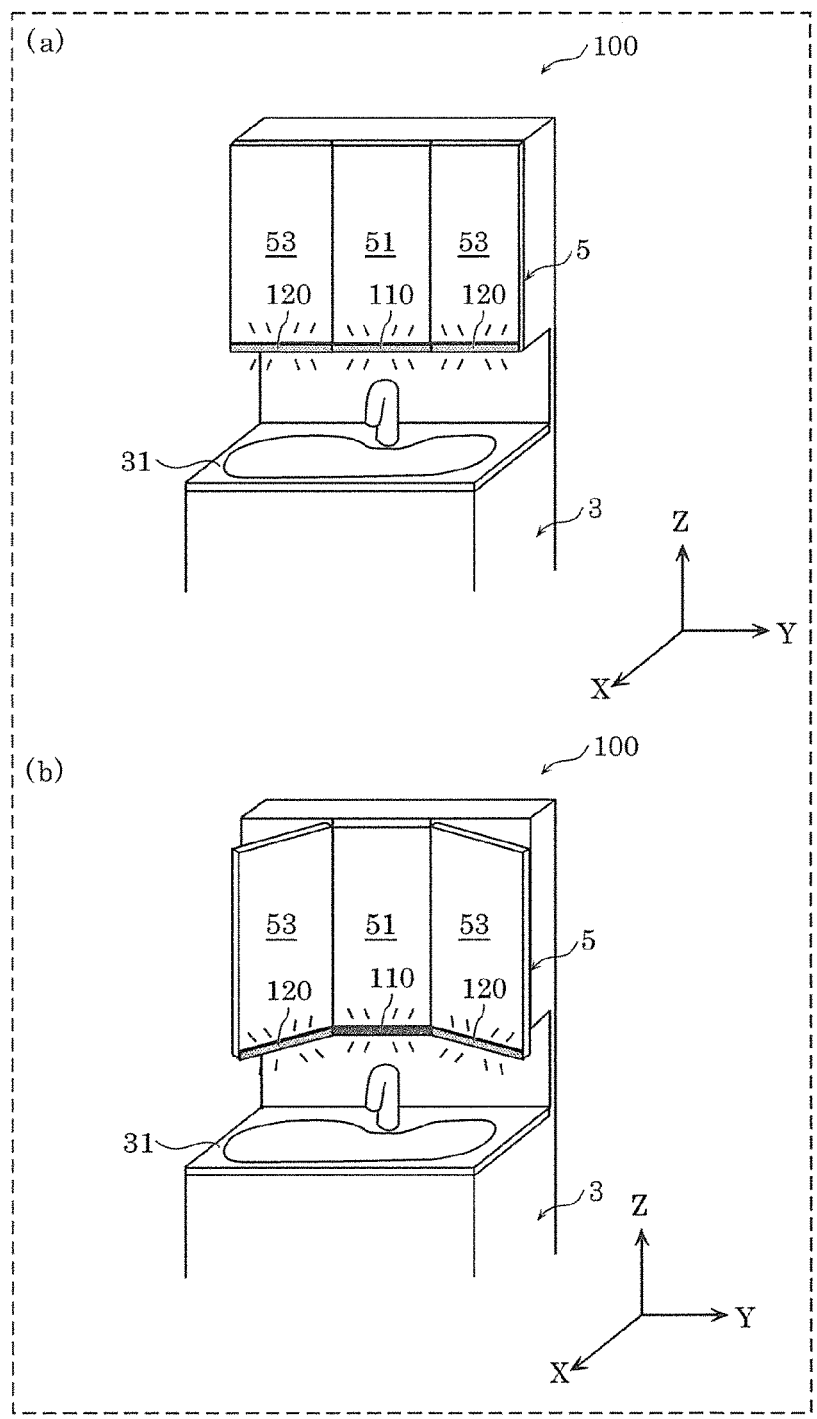
FIG. 2 illustrates a partial enlarged schematic view (a) of the mirror apparatus according to the embodiment when side mirrors are not rotated, and a partial enlarged schematic view (b) of the mirror apparatus according to the embodiment when side mirrors are rotated.
Figure 3:
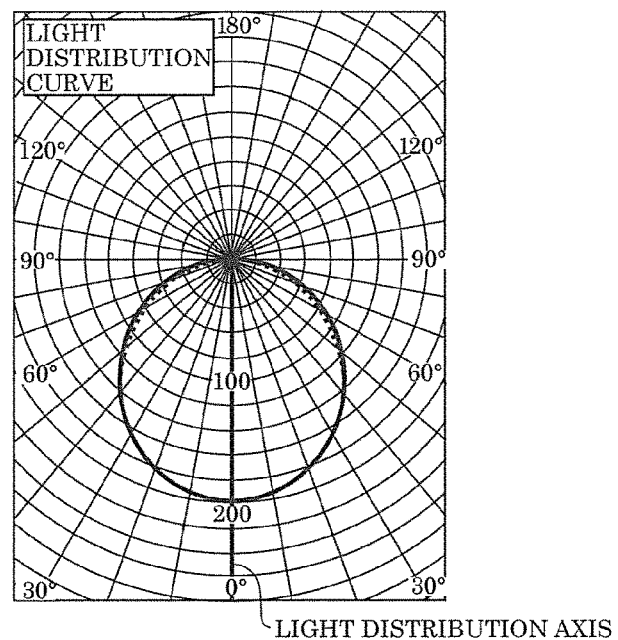
FIG. 3 is a diagram illustrating light distribution curves of light emitted from a treatment luminaire according to the embodiment.
Figure 4:
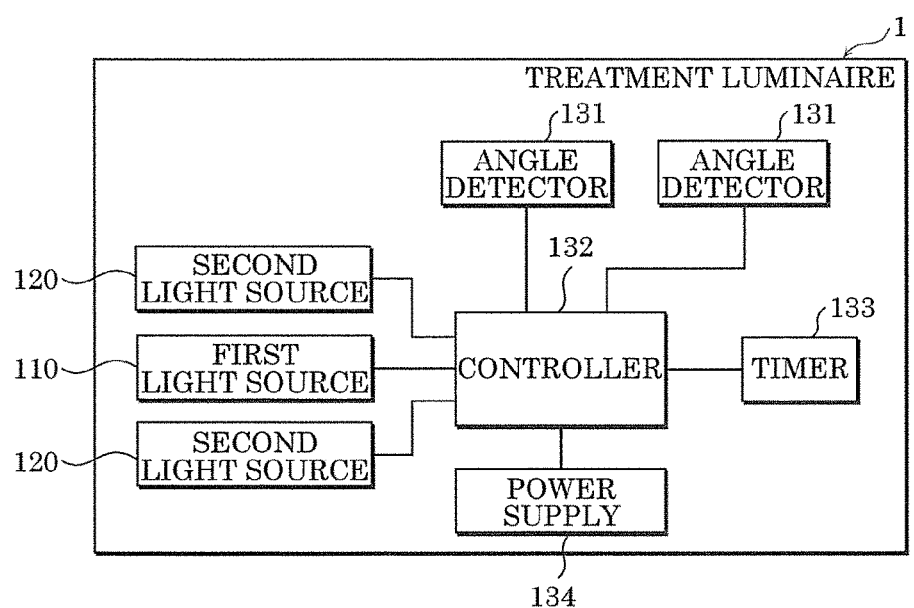
FIG. 4 is a block diagram illustrating the treatment luminaire according to the embodiment.
Figure 5:
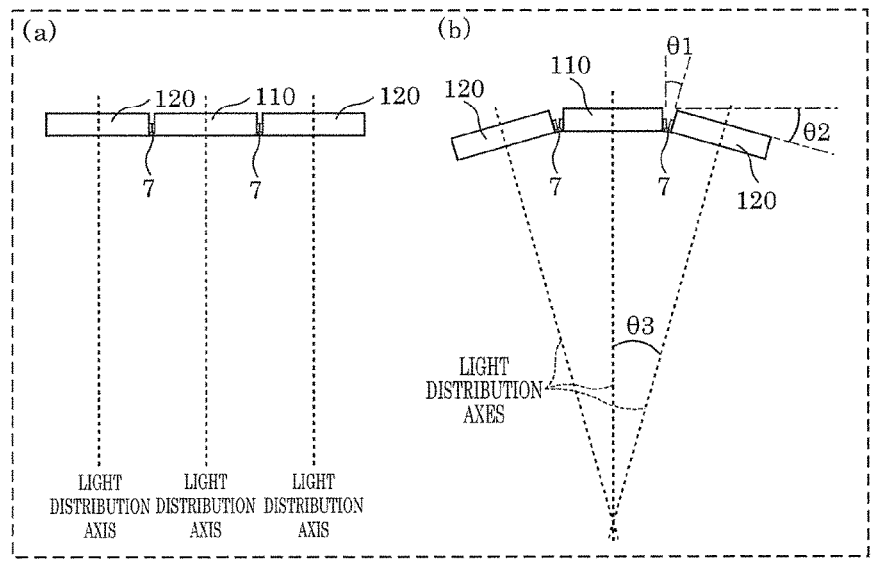
FIG. 5 illustrates a schematic view (a) of a case where the light distribution axis of a first light source and the light distribution axes of second light sources are parallel to each other, and a schematic view (b) of angles between the light distribution axis of the first light source and the light distribution axes of the second light sources.

FIG. 1 is a schematic view of mirror apparatus 100 according to an embodiment. In FIG. 2, (a) is a partial enlarged schematic view of mirror apparatus 100 according to the embodiment when side mirrors 53 are not rotated. In FIG. 2, (b) is a partial enlarged schematic view of mirror apparatus 100 according to the embodiment when side mirrors 53 are rotated. FIG. 3 is a diagram illustrating light distribution curves of light emitted from treatment luminaire 1 according to the embodiment. FIG. 4 is a block diagram illustrating treatment luminaire 1 according to the embodiment. In FIG. 5, (a) is a schematic view illustrating a case where the light distribution axis of first light source 110 and the light distribution axes of second light sources 120 are parallel to each other. In FIG. 5, (b) is a schematic view illustrating angles between the light distribution axis of first light source 110 and the light distribution axes of second light sources 120.

FIG. 1 shows X, Y, and Z directions by defining that the direction in which the light distribution axis of first light source 110 extends is the positive direction of X axis, that the side of mirror cabinet 5 with respect to cabinet body 3 is on the positive direction of Z axis, and that the direction orthogonal to the positive direction of Z axis and the positive direction of X axis is the positive direction of Y axis. All of these directions shown in FIG. 1 are shown correspondingly as the respective directions in FIG. 2. This also applies to the diagrams following FIG. 2.

As illustrated in FIG. 1, mirror apparatus 100 is an apparatus for mirroring the appearance of a user and is disposed in a room of a home or the like, and is, for example, a washstand, a dresser with three mirrors, or the like. This embodiment takes a washstand as an example. Mirror apparatus 100 can irradiate the user with light when the user adjusts his or her appearance by, for example, putting on makeup, changing clothes, washing his or her face.

As illustrated in FIG. 1, mirror apparatus 100 includes: cabinet body 3; mirror cabinet 5; a plurality of hinges 7 (examples of adjusters); and treatment luminaire 1 illustrated in FIG. 4.

Cabinet body 3 is a washstand having wash bowl 31 with a faucet embedded therein. Using wash bowl 31 with the faucet, the user can perform operations such as washing his or her face, hands, hair, etc. Cabinet body 3 includes a housing space for housing goods etc. necessary for washing his or her face and hair, putting on makeup, etc. Cabinet body 3 includes doors, drawers, etc. for opening and closing the housing space.

Mirror cabinet 5 is mounted on cabinet body 3 to compose the washstand. Mirror cabinet 5 is vertically disposed above cabinet body 3 on the positive side of Z axis.

Mirror cabinet 5 includes: center mirror 51 (an example of a first mirror); and two side mirrors 53 (examples of second mirrors).

Center mirror 51 is vertically fixed on mirror cabinet 5 such that center mirror 51 is disposed between two side mirrors 53 to be approximately parallel to the Z-axis direction and the Y-axis direction. It is to be noted that center mirror 51 may open or close in the horizontal direction.

One of side mirrors 53 is vertically held by mirror cabinet 5 such that the one of side mirrors 53 is disposed on the positive side in the Y-axis direction with respect to center mirror 51, to be approximately parallel to the Z-axis direction and the Y-axis direction. As illustrated in (a) and (b) of FIG. 2, the one of side mirrors 53 is mounted rotatably in the horizontal direction assuming, as the center axis, the Z-axis direction of one of the side edges (the edge on the positive side in the Y-axis direction) of center mirror 51.

The other one of side mirrors 53 is vertically held by mirror cabinet 5 such that the one of side mirrors 53 is disposed on the negative side in the Y-axis direction with respect to center mirror 51, to be approximately parallel to the Z-axis direction and the Y-axis direction. The one of side mirrors 53 is mounted rotatably in the horizontal direction assuming, as the center axis, the Z-axis direction of the other side edge (the edge on the negative side in the Y-axis direction) of center mirror 51.

Treatment luminaire 1 includes first light source 110 and two second light sources 120.

First light source 110 is disposed between two second light sources 120, and emits light forward (the positive side in the X-axis direction) of mirror cabinet 5. First light source 110 is disposed on a surface of center mirror 51 to irradiate the user with light when the user uses mirror apparatus 100. The surface is positioned on the positive side in the X-axis direction. Although first light source 110 is disposed at the edge positioned on the negative side in the Z-axis direction with respect to center mirror 51 in this embodiment, it should be noted that first light source 110 may be held on center mirror 51 via a holding member.

In this embodiment, first light source 110 is disposed at the edge positioned on the negative side in the Z-axis direction with respect to center mirror 51. First light source 110 emits light in the positive direction of X axis that is approximately parallel to the light distribution axis. Here, the light distribution axis is a straight line at the 0-degree direction of a light distribution curve illustrated in FIG. 3. In other words, the light distribution axis is a straight line which connects the maximum value (the portion at which intensity is strongest) of the light distribution curve and first light source 110.

As illustrated in (a) and (b) of FIG. 2, one of second light sources 120 is disposed on the positive side in the Y-axis direction with respect to first light source 110, and emits light forward (the positive side in the X-axis direction) of mirror cabinet 5. In other words, the one of second light sources 120 is held by one of side mirrors 53 so as to irradiate the user with light when the user uses mirror apparatus 100.

The other one of second light sources 120 is disposed on the negative side in the Y-axis direction with respect to first light source 110, and emits light forward (the positive side in the X-axis direction) of mirror cabinet 5. In other words, the other one of second light sources 120 is held by the other one of side mirrors 53 so as to irradiate the user with light when the user uses mirror apparatus 100.

In this embodiment, second light sources 120 are disposed at the edges on the negative side in the Z-axis direction with respect to side mirrors 53. In (a) of FIG. 2 in which side mirrors 53 are not rotating in the horizontal direction, second light sources 120 emit light in the positive direction of X axis. Although second light sources 120 are directly held by side mirrors 53 in this embodiment, it should be noted that second light sources 120 may be held by side mirrors 53 via holding members.

Each of first light source 110 and second light sources 120 selectively emits treatment light or illumination light. More specifically, each of first light source 110 and second light sources 120 irradiates the user with treatment light, illumination light, and both of treatment light and illumination light.

Here, the treatment light is light which provides an effect of adjusting the vital rhythm of the user. The treatment light is light including blue light having a wavelength in a range from 380 nm to 500 nm. It is particularly desirable that the treatment light include light having a wavelength around 480 nm. The illumination light is visible light, for example, in a range from 380 nm to 780 nm. The illumination light is for illuminating a surrounding area, and is not for intentionally giving a user treatment unlike the treatment light.

Each of first light source 110 and second light sources 120 may be, for example, a light emitting diode (LED) element, a semiconductor light emitting element such as a semiconductor laser, or another solid-state light emitting element including an electro-luminescent (EL) element that is for example an organic EL element or an inorganic EL element.

Hinges 7 are fixed at center mirror 51 and two side mirrors 53 rotatably in the horizontal direction. Hinges 7 are members for adjusting the angles of respective side mirrors 53 with respect to center mirror 51, and with which it is possible to adjust the crossing angles between the light distribution axis of first light source 110 and the light distribution axes of second light sources 120. Two hinges 7 are mounted at the edges on the positive side in the Y-axis direction with respect to center mirror 51. One of hinges 7 fixes (connects) a corresponding one of side mirrors 53 to center mirror 51 on the positive side in the Z-axis direction with respect to center mirror 51 and the corresponding one of side mirrors 53. The other one of hinges 7 fixes (connects) the corresponding one of side mirrors 53 to center mirror 51 on the negative side in the Z-axis direction with respect to center mirror 51 and the corresponding one of side mirrors 53.

Two hinges 7 are mounted at the edges on the negative side in the Y-axis direction with respect to center mirror 51. One of hinges 7 fixes the other one of side mirrors 53 to center mirror 51 on the positive side in the Z-axis direction with respect to center mirror 51 and the other one of side mirrors 53. The other one of hinges 7 fixes the other one of side mirrors 53 to center mirror 51 on the negative side in the Z-axis direction with respect to center mirror 51 and the other one of side mirrors 53.

In this way, in this embodiment, two side mirrors 53 are supported rotatably in the horizontal direction with respect to center mirror 51 using these four hinges 7.

As illustrated in FIG. 4, treatment luminaire 1 further includes: a plurality of angle detectors 131; controller 132; timer 133; and power supply 134.

Angle detectors 131 are each an angle detecting sensor for detecting a rotation angle of hinge 7 (the angle of hinge 7), and is, for example, a rotary encoder. Rotary encoder outputs the detected angle of hinge 7 to controller 132. As an example of detecting the angle of hinge 7, it is also possible to detect the angle of hinge 7 according to a rotation of hinge 7 by disposing, on hinge 7, the rotary encoder which rotates according to the rotation of hinge 7. It is also good to fix integrally the rotation axis of hinge 7 and the rotation axis of the rotary encoder so that the rotation axis of the rotary encoder rotates together with the rotation of hinge 7. In this way, rotary encoder is capable of detecting the angle of hinge 7 and outputting a signal indicating the angle to controller 132.

In this embodiment, one of angle detectors 131 is provided to hinge 7 on the positive side in the Y-axis direction with respect to center mirror 51 and the other one of angle detectors 131 is provided to hinge 7 on the negative side in the Y-axis direction with respect to center mirror 51.

As illustrated in (a) and (b) of FIG. 5, angle $\theta1$ is an angle formed when hinge 7 rotated in the horizontal direction, for example, from the angle illustrated in (a) of FIG. 5 to the angle illustrated (b) in FIG. 5. In other words, hinge 7 rotated in the horizontal direction by the amount of rotation of side mirrors 53 with respect to a surface of center mirror 51. Angle $\theta1$ of hinge 7 equals to angle $\theta2$ of surfaces of side mirrors 53 with respect to the surface of center mirror 51, and equals to crossing angle $\theta3$ between the light distribution axis of first light source 110 and the light distribution axis of each of second light sources 120. For this reason, angle $\theta1$ of hinge 7, angle $\theta2$ of the surface of each of side mirrors 53 with respect to center mirror 51, and crossing angle $\theta3$ between the light distribution axis of first light source 110 and the light distribution axis of each of second light sources 120 is used in the same meaning. For example, as in (a) of FIG. 5, angle $\theta1$ of hinge 7 is 0 degree when the surface of center mirror 51 and the surfaces of side mirrors 53 are approximately parallel to each other (the light distribution axis of first light source 110 and the light distribution axis of each of second light sources 120 is parallel to each other).

As illustrated in FIG. 4, controller 132 includes a control circuit, etc. The control circuit controls operations to be performed by first light source 110, second light sources 120, power supply 134 etc. Controller 132 includes a lighting control circuit, and controls turning on and off of first light source 110 and second light sources 120. More specifically, controller 132 controls start and stop of supply of power from power supply 134. For example, when an operation interface receives a turning-on operation, controller 132 supplies power from power supply 134 to first light source 110 and second light sources 120 to turn on first light source 110 and second light sources 120. When the operation interface receives a turning-off operation, controller 132 stops supply of power from power supply 134 to first light source 110 and second light sources 120 to turn off first light source 110 and second light sources 120.

Controller 132 controls dimming and toning of first light source 110 and second light sources 120. Specifically, controller 132 performs dimming by increasing or decreasing an output of current to first light source 110 and second light sources 120. Controller 132 performs toning by changing the balance of supply of current to first light source 110 and supply of current to second light sources 120. Controller 132 increases or decreases supply of current to each of first light source 110 and second light sources 120 by, for example, PWM control.

Controller 132 switches the operation mode of at least one of first light source 110 and second light sources 120 between a normal mode (an example of a first mode) and a treatment mode (an example of a second mode) different from the normal mode, according to the angle of hinge 7 detected by angle detector 131. Specifically, when controller 132 detected that the angle of hinge 7 reached or exceeded a predetermined angle through angle detector 131, controller 132 switches the operation mode from the normal mode to the treatment mode. When controller 132 detected that the angle of hinge 7 was reduced below the predetermined angle through angle detector 131, controller 132 switches the operation mode from the treatment mode to the normal mode.

The normal mode is a mode in which first light source 110 and second light sources 120 emit illumination light for illuminating a surrounding area. In the normal mode, controller 132 causes first light source 110 and second light sources 120 to turn on. The treatment mode is a mode in which treatment light for therapeutic use is emitted, and mainly the amount of blue light from second light sources 120 is increased.

When controller 132 causes first light source 110 and second light sources 120 to operate in the treatment mode, controller 132 controls the operations by first light source 110 and second light sources 120 according to the crossing angles between the light distribution axis of first light source 110 and the light distribution axes of second light sources 120. Specifically, according to the crossing angles, controller 132 turns on second light sources 120 in such a manner that second light sources 120 emit brighter treatment light in the treatment mode than illumination light in the normal mode. For example, with an increase in the crossing angles, controller 132 turns on second light sources 120 in such a manner that second light sources 120 emit brighter treatment light in the treatment mode than illumination light in the normal mode.

In addition, according to the crossing angles, controller 132 turns on first light source 110 in such a manner that first light source 110 emits darker treatment light in the treatment mode than illumination light in the normal mode. For example, with an increase in the crossing angles, controller 132 turns on first light source 110 in such a manner that first light sources 110 emits darker treatment light in the treatment mode than illumination light in the normal mode.

When controller 132 causes first light source 110 and second light sources 120 to operate in the treatment mode, controller 132 changes the output of light from the at least one of first light source 110 and second light sources 120 according to the crossing angle(s) between the light distribution axis of first light source 110 and the light distribution axis/axes of second light source(s) 120. For example, when controller 132 causes first light source 110 and second light sources 120 to operate in the treatment mode, controller 132 may cause the at least one of first light source 110 and second light sources 120 to increase the brightness of light with an increase in the angle(s).

Controller 132 turns on second light sources 120 in such a manner that the ratio of blue light included in the treatment light emitted by second light sources 120 in the treatment mode is larger than the ratio of blue light included in the illumination light emitted by first light source 110 in the normal mode or the ratio of blue light included in the illumination light emitted by second light source 120 in the normal mode. In other words, the percentage of the amount of blue light with respect to the total amount of light emitted by second light sources 120 in the treatment mode is larger than the percentage of the amount of blue light with respect to the total amount of light emitted by first light source 110 in the normal mode or the percentage of the amount of blue light with respect to the total amount of light emitted by second light sources 120 in the normal mode.

Controller 132 turns on second light sources 120 in such a manner that the amount of blue light included in the treatment light emitted by second light sources 120 in the treatment mode is larger than the amount of blue light included in the illumination light emitted by first light source 110 in the normal mode or the amount of blue light included in the illumination light emitted by second light sources 120 in the normal mode. In other words, second light sources 120 in the treatment mode emit light including blue light the amount of which is greater than each of the amount of blue light included in illumination light emitted by first light source 110 and the amount of blue light included in illumination light emitted by second light sources 120 in the normal mode.

Controller 132 turns on second light sources 120 in such a manner that second light sources 120 emit brighter treatment light in the treatment mode than illumination light in the normal mode. In other words, controller 132 causes second light sources 120 to emit a greater amount of blue light in the treatment mode than illumination light in the normal mode.

Controller 132 is implemented as a microcomputer, a processor, or an exclusive circuit which controls, for example, the value of current to be supplied to first light source 110 and second light sources 120 according to an input signal.

Treatment luminaire 1 may include an operation interface. The operation interface may include a light selection button, a mode selection button, a light emission switch, a treatment light setting button arranged side by side. The light selection button may be a button for selecting treatment light or illumination light to be emitted. The mode selection button may be a button for selecting the normal mode or the treatment mode. The light emission switch may be a switch for causing first light source 110 and second light sources 120 to emit light. The light setting button may be a button for allowing a user to selectively set intensity levels of treatment light and illumination light.

The operation interface may be a mechanical push button, or a touch panel of an electrostatic capacitance type. The operation interface may be operable by a remote controller.

Timer 133 is connected to controller 132, and is a device for measuring time during which first light source 110 and second light sources 120 emit treatment light. Timer 133 transmits the measured time to controller 132. As the setting of timer 133, the time in which the user receives treatment can be set by the user through the operation interface.

It should be noted that treatment luminaire 1 may include non-volatile storage device for storing time set in timer 133. As the storage, a semiconductor memory such as a flash memory and an EEPROM is employed.

Power supply 134 includes: a rectifier circuit of a diode bridge type which converts alternating-current power supplied from a system power to direct-current power; and a DC-DC converter. Power supply 134 may be implemented as a single integrated circuit (IC) having functions equivalent to functions of the rectifier circuit and the DC-DC converter. Power supply 134 supplies power to first light source 110 and second light sources 120 etc. under control of controller 132.

[Operations]

Operations performed by treatment luminaire 1 and mirror apparatus 100 according to this embodiment are described with reference to FIG. 6.

Figure 6:
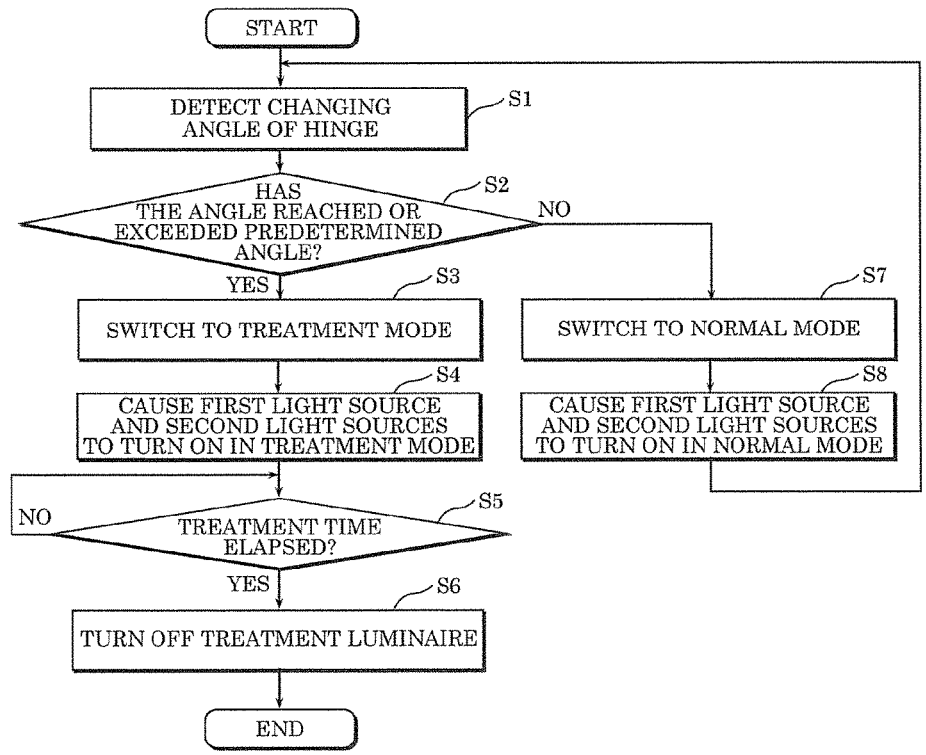
FIG. 6 is a flowchart illustrating operations performed by the treatment luminaire according to the embodiment.

FIG. 6 is a flowchart illustrating operations performed by treatment luminaire 1 according to the embodiment.

Although two angle detectors 131 for detecting the angles of two hinges 7 are provided in this embodiment, one of hinges 7 and a corresponding one of angle detectors 131 are described in the following flow. The other one of hinges 7 is operated and the corresponding one of angle detectors 131 operates in the same manner, and thus the same descriptions are not repeated.

When a user turns on and activates the power of treatment luminaire 1, the flow in FIG. 6 is started.

As illustrated in FIG. 6, first, one of angle detectors 131 detects a changing angle of a corresponding one of hinges 7 (S1).

Next, controller 132 detects whether or not the changing angle of hinge 7 has reached or exceeded a predetermined angle (S2).

Next, when the changing angle of hinge 7 has reached or exceeded the predetermined angle (YES in S2), controller 132 switches the operation modes of first light source 110 and second light sources 120 to a treatment mode (S3).

Next, controller 132 causes first light source 110 and second light sources 120 to turn on in the treatment mode (S4). Specifically, in the treatment mode, controller 132 turns on second light sources 120 in such a manner that second light sources 120 emit treatment light which is brighter than illumination light in the normal mode and which includes a greater ratio or amount of blue light compared to illumination light in the normal mode. In addition, controller 132 turns on first light source 110 in such a manner that first light source 110 emits darker treatment light in the treatment mode than illumination light in the normal mode.

Next, controller 132 determines whether or not treatment time has elapsed from the start of the treatment mode (S5). The treatment time is set in advance in timer 133.

When controller 132 determined that the set treatment time was elapsed (YES in S5), controller 132 turns off the power of treatment luminaire 1 (S6). At this time, the flow ends. It should be noted that, in this flowchart, a transition may be made to Step S7 for switching to the normal mode after the process in Step S5 is performed.

When controller 132 determined that the set treatment time was not elapsed (NO in S5), a return is made to Step S5.

When the changing angle of hinge 7 is not reduced below the predetermined angle (NO in S2), controller 132 switches operation modes to normal mode (S7)

Next, controller 132 controls first light source 110 and second light sources 120 according to the normal mode (S8). First light source 110 and second light sources 120 are turned on in the normal mode. Subsequently, a return is made to Step S1.

In this flow, the activation of treatment luminaire 1 is finished when the user turns off the power of treatment luminaire 1.

[Evaluation Result]

Figure 7:
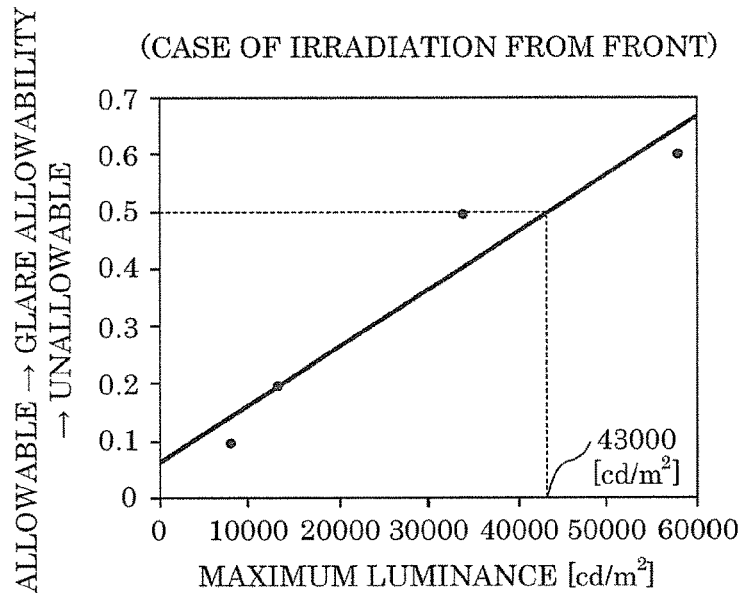
FIG. 7 is a graph illustrating the relationship between the maximum luminance and glare allowability as a result of an evaluation test in which light is applied to subjects from front.
Figure 8:
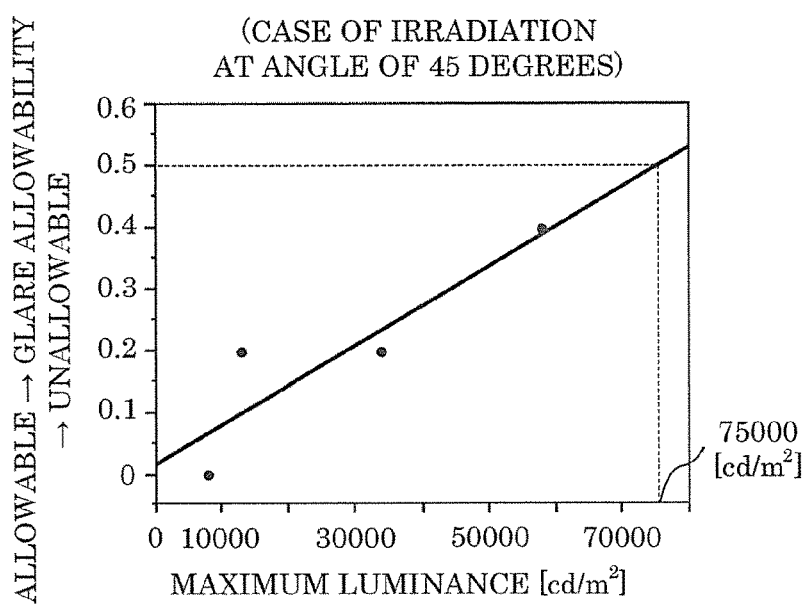
FIG. 8 is a graph illustrating the relationship between the maximum luminance and glare allowability as a result of an evaluation test in which light is applied to subjects at an angle of 45 degrees.

The Inventors evaluated glare allowability as shown in FIGS. 7 and 8.

FIG. 7 is a graph illustrating the relationship between the maximum luminance and glare allowability as a result of an evaluation test in which light is applied to a subject from front. FIG. 8 is a graph illustrating the relationship between the maximum luminance and glare allowability as a result of an evaluation test in which light is applied to a subject at an angle of 45 degrees.

Each of FIGS. 7 and 8 shows the result of an evaluation test of glare allowability performed under environmental illumination of 750 lx and with eleven males as subjects. The subjects are non-handicapped men. Such evaluation tests were performed under the condition combinations of: the area of light emitters selected from 100 cm$^2$ and 200 cm$^2$, illuminance of subjects' faces selected from 2000 lx, 3000 lx, and 4000 lx, and irradiation time that is 30 seconds.

In the evaluation test, a questionnaire including questions for asking, for each condition combination, "Is the glare allowable?" was performed. Each question can be answered by selecting one of the following four answer options: "Yes", "Rather Yes", "Rather No", and "Definitely No". For each condition combination, the answers "Yes" and "Rather Yes" are represented as 0 and the answers "Rather No" and "Definitely No" are represented as 1, and the values indicating the answers of the eleven subjects are averaged.

The results in FIGS. 7 and 8 show that the subjects can bear the glare in the case of FIG. 8 than in the case of FIG. 7. FIG. 7 shows that the maximum luminance which can be borne by 50 percent of the subjects is approximately 43000 [cd/m$^2$]. FIG. 8 shows that the maximum luminance which can be borne by 50 percent of the subjects is approximately 75000 [cd/m$^2$]. In other words, these results show that humans are less dazzled by light emitted diagonally toward them than light emitted toward them from front (can bear the glare of the former light more than the latter light).

[Effects]

Next, effects provided by treatment luminaire 1 and mirror apparatus 100 according to the embodiment are described.

As described above, treatment luminaire 1 according to the embodiment includes: first light source 110; second light sources 120; hinges 7 for adjusting the crossing angles between the light distribution axis of first light source 110 and the light distribution axes of second light sources 120; and controller 132 which switches, according to the crossing angles, the operation modes of first light source 110 and second light sources 120 between a normal mode for emitting illumination light for illuminating a surrounding area and a treatment mode for emitting treatment light for therapeutic use.

With hinges 7, it is possible to change the crossing angles between the light distribution axis of first light source 110 and the light distribution axes of second light sources 120. Since controller 132 switches operation modes between the normal mode and the treatment mode according to the crossing angles between the light distribution axis of first light source 110 and the light distribution axes of second light sources 120, it is only necessary for the user to adjust the angle(s) in order to adjust the amounts of light to be emitted from first light source 110 and second light sources 120.

Accordingly, the user of treatment apparatus 1 is less dazzled by light emitted from treatment luminaire 1.

Controller 132 in treatment luminaire 1 according to this embodiment turns on second light sources 120 in such a manner that second light sources 120 emit brighter treatment light in the treatment mode than illumination light in the normal mode.

In this way, it is possible to cause second light sources 120 to emit a large amount of treatment light which provides therapeutic effects in treatment mode compared to the amount of illumination light emitted by second light sources 120 in the normal mode. For this reason, the treatment light in the treatment mode is suitable for treatment of the user.

Controller 132 in treatment luminaire 1 according to this embodiment turns on first light sources 110 in such a manner that first light source 110 emits darker treatment light in the treatment mode than illumination light in the normal mode.

In this way, since first light source 110 is turned on to emit the darker illumination light in the normal mode than the treatment light in the treatment mode, light emitted toward the user from front is reduced in the treatment mode. For this reason, the user is less dazzled by the light in the treatment mode.

In treatment luminaire 1 according to this embodiment, the ratio of the amounts of blue light emitted by second light sources 120 in the treatment mode is larger than the ratio of the amount of blue light emitted by first light source 110 in the normal mode or the ratio of the amounts of blue light emitted by second light sources 120 in the normal mode.

In this way, since the ratio of the amounts of blue light in the treatment light emitted by second light sources 120 is large in the treatment mode, the treatment light is suitable for giving the user treatment.

In treatment luminaire 1 according to this embodiment, the amounts of blue light included in the treatment light emitted by second light sources 120 in the treatment mode is larger than the amount of blue light included in the illumination light emitted by first light source 110 in the normal mode or the amounts of blue light included in the illumination light emitted by second light sources 120 in the normal mode.

In this way, since the amounts of blue light included in the treatment light emitted by second light sources 120 in the treatment mode are large, second light sources 120 can emit the large amount of treatment light that provides therapeutic effects. For this reason, the treatment light in the treatment mode is suitable for treatment of the user.

In treatment luminaire 1 according to this embodiment, when controller 132 causes at least one of first light source 110 and second light sources 120 to operate in the treatment mode, controller 132 changes the output of light from the at least one of first light source 110 and second light sources 120 to according to the angle(s) between the light distribution axis of first light source 110 and the light distribution axis/axes of second light source(s) 120.

In this way, since the output light from the at least one of first light source 110 and second light sources 120 changes according to the angle(s), for example, it is possible to cause first light source 110 to emit brighter light and cause second light source(s) 120 to emit darker light with an increase in the angle(s). For this reason, since the user is less dazzled by light when the angle(s) is/are large, it is possible to actively emit the treatment light by increasing the amount of light emitted by first light source 110 and the user is less dazzled by the light because the amounts of light emitted by second light sources 120 are reduced.

In treatment luminaire 1 according to this embodiment, two second light sources 120 are arranged on different sides of first light source 110.

In this way, since two second light sources 120 are arranged, it is possible to irradiate the user with the treatment light from the both sides, which increases the therapeutic effects.

In addition, in treatment luminaire 1 according to this embodiment, when the light distribution axis of at least one of the two second light sources 120 is tilted more than a threshold angle with respect to the light distribution axis of first light source 110, controller 132 switches the operation modes of first light source 110 and the at least one of second light sources 120 between the normal mode and the treatment mode.

In addition, in treatment luminaire 1 according to this embodiment, when the light distribution axis of the at least one of two second light sources 120 is tilted more than the threshold angle with respect to the light distribution axis of first light source 110, controller 132 changes the outputs of light from first light source 110 and the at least one of second light sources 120 according to the crossing angle between the light distribution axis of first light source 110 and the light distribution axis of the at least one of second light sources 120.

In addition, in treatment luminaire 1 according to this embodiment, when controller 132 causes the at least one of first light source 110 and second light sources 120 to operate in the treatment mode, controller 132 causes the at least one of first light source 110 and second light sources 120 to increase an output of light with an increase in the angle between the light distribution axis of first light source 110 and the axis of a corresponding one of second light sources 120.

In addition, in treatment luminaire 1 according to this embodiment, the treatment light is light including blue light having a peak wavelength in a range from 380 nm to 500 nm, and the illumination light is visible light having a peak wavelength in a range from 380 nm to 780 nm.

In addition, in treatment luminaire 1 according to this embodiment, the maximum luminance of light emitted by first light source 110 is 43000 cd/m$^2$ in the treatment mode, and the maximum luminance of light emitted by second light sources 120 is 75000 cd/m$^2$ in the treatment mode when the light distribution axis of the at least one of second light sources 120 are tilted by 45 degrees with respect to the light distribution axis of first light source 110.

In addition, treatment luminaire 1 according to this embodiment includes: first light source 110 which selectively emits illumination light for illuminating a surrounding area and treatment light for therapeutic use; second light sources 120 which selectively emit illumination light for illuminating a surrounding area and treatment light for therapeutic use; hinges 7 for changing the crossing angles between the light distribution axis of first light source 110 and the light distribution axes of second light sources 120; and controller 132 which switches the operation modes of first light source 110 and second light sources 120 between the normal mode and the treatment mode according to the angles.

In addition, mirror apparatus 100 according to this embodiment includes: treatment luminaire 1; center mirror 51 on which first light source 110 is disposed; and two side mirrors 54 arranged on different sides of center mirror 51. Each of side mirrors 53 is provided with a corresponding one of second light sources 120.

In this way, since first light source 110 and second light sources 120 are provided to center mirror 51 and side mirrors 53, the light distribution axes of second light sources 120 can be changed by rotation of side mirrors 53 in a user-friendliness manner.

Mirror apparatus 100 according to this embodiment further includes, as adjusters, hinges 7 each of which connects center mirror 51 and a corresponding one of two side mirrors 53. Mirror apparatus 100 further includes angle detectors 131 each of which detects, as a changing angle of a corresponding one of hinges 7, the crossing angle between the light distribution axis of first light source 110 and the light distribution axis of a corresponding one of second light sources 120. Controller 132 switches the operation modes of first light source 110 and second light sources 120 according to the changing angle of hinge 7 detected by angle detector 131.

In this way, angle detector 131 detects the angle of hinge 7 and controller 132 switches between the normal mode and the treatment mode according to the angle. Thus, it is only necessary for the user to adjust the angle of hinge 7 in order to adjust the amounts of light to be emitted from first light source 110 and second light sources 120. Accordingly, treatment luminaire 1 is user-friendly.

In addition, in mirror apparatus 100 according to this embodiment, controller 132 switches operation modes from the normal mode to the treatment mode when angle detector 131 detected that the angle of hinge 7 reached or exceeded a predetermined angle, while controller 132 switches operation modes from the treatment mode to the normal mode when angle detector 131 detected that the angle of hinge 7 was reduced below the predetermined angle.

In addition, mirror apparatus 100 according to this embodiment further includes: timer 133 which measures irradiation time during which first light source 110 and second light sources 120 emit treatment light. Controller 132 emits treatment light according to time set in timer 133.

In addition, in mirror apparatus 100 according to this embodiment, first light source 110 is disposed at an edge of first mirror. Each of second light sources 120 is disposed at an edge of a corresponding one of second mirrors.

Variation of Embodiment

[Configuration]

Hereinafter, a configuration of mirror apparatus 200 according to this variation of the embodiment is described.

Figure 9:
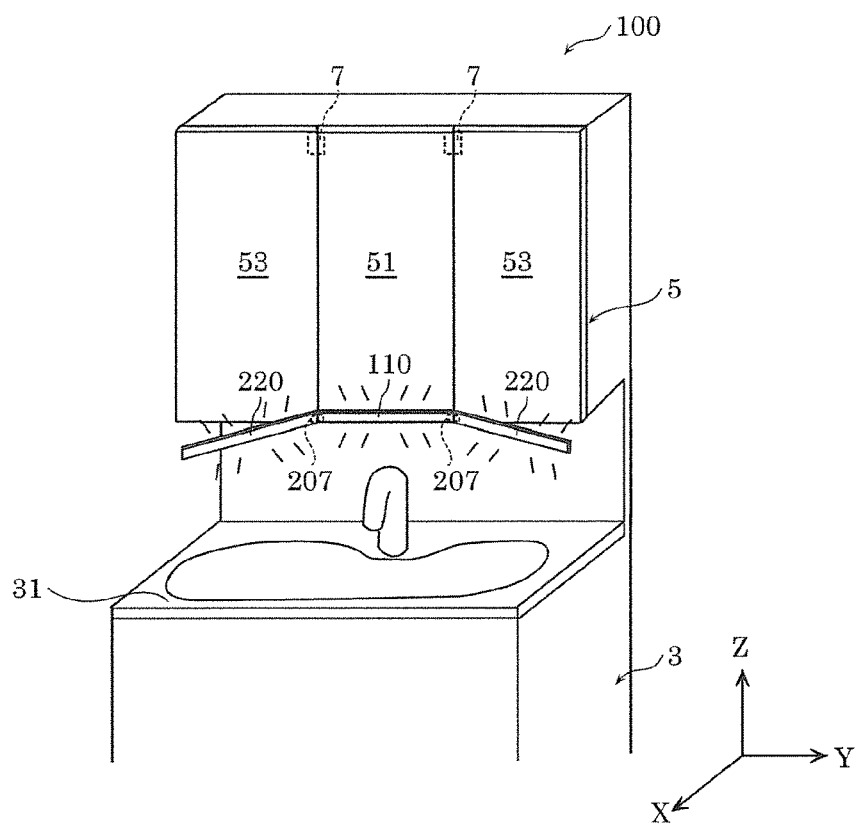
FIG. 9 is a partial enlarged schematic view of the mirror apparatus according to a variation of the embodiment when second light sources are rotated.

FIG. 9 is a partial enlarged schematic view of mirror apparatus 200 according to this variation when second light sources 220 are rotated.

This variation differs from the embodiment in that second light sources 220 rotate independently in the horizontal direction.

Mirror apparatus 200 is configured in the same manner as mirror apparatus 100 according to the embodiment except for the above difference. The same elements are assigned the same reference signs, and the detailed descriptions of such elements are not repeated.

As illustrated in FIG. 9, second light sources 220 are attached to center mirror 51 or side mirrors 53 via hinge 207. Second light sources 220 are mounted rotatably in the horizontal direction about the axis in the Z-axis direction. Second light sources 220 rotate independently with respect to side mirrors 53. Angle detector 131 detects a changing angle of hinge 207.

It should be noted that first light source 110 may also be rotatable via a hinge.

Effects provided by mirror apparatus 200 are the same as those provided by mirror apparatus 100 according to the embodiment, and thus the same effects are not described in detail repeatedly.

Other Variations

Although the present disclosure has been provided above based on the embodiment and the variation of the embodiment, the present disclosure is not limited to the embodiment and the variation of the embodiment.

Figure 10:
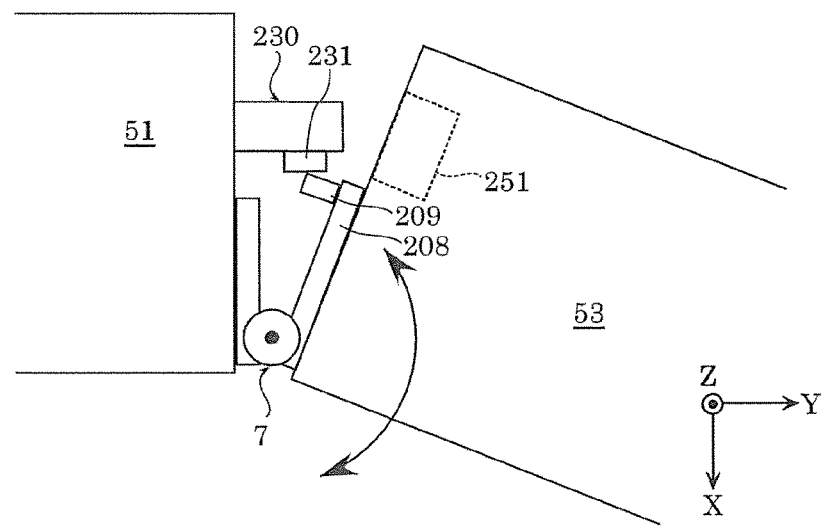
FIG. 10 is a schematic diagram illustrating an example where the angle of one of the side mirrors is detected in the mirror apparatus according to a variation.

FIG. 10 is a schematic diagram illustrating an example where the angles of side mirrors are detected in the mirror apparatus according to the variation. FIG. 10 is a diagram of a mirror apparatus when seen from the positive side of Z axis. As illustrated in FIG. 10, in the above embodiment, as another example where the angle of hinge 7 is detected, micro switch 230 may be disposed between side mirror 53 and center mirror 51 to detect that the angle of hinge 7 has reached or exceeded a predetermined angle. More specifically, micro switch 230 with switching portion 231 is attached to a side surface of center mirror 51 positioned on the positive side in the Y-axis direction of center mirror 51. Center mirror 51 has groove 251 for housing micro switch 230 when the angle of side mirror 53 is 0 degree. Protrusion 209 is formed on metal portion 208 of hinge 7 in such a manner that protrusion 209 protrudes in the normal direction from the positive side in the Y-axis direction of side mirror 53. Hinge 7 is rotated by rotation of side mirror 53, and thus when the angle of hinge 7 has reached or exceeded the predetermined angle, protrusion 209 of metal portion 208 of hinge 7 presses switch portion 231 of micro switch 230. In this way, angle detector 131 can detect that the angle of hinge 7 reached or exceeded the predetermined angle. It should be noted that this method is a non-limiting example of a method for detecting an angle of hinge 7.

In addition, in the above embodiment, light distribution lenses may be disposed on the positive side in the X-axis direction of second light sources. This light distribution lenses may be mounted to be rotated by other hinges with respect to second light sources and side mirrors. Angle detectors detect rotating angles of the light distribution lenses. A controller may switch operation modes between a normal mode and a treatment mode according to changing angles of the hinges detected by the angle detectors.

While the foregoing has described one or more embodiments and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present teachings.

What is claimed is:

1. A treatment luminaire, comprising:
a first light source;
a second light source;
an adjuster for adjusting a crossing angle between a light distribution axis of the first light source and a light distribution axis of the second light source; and
a controller which switches, according to the crossing angle, operation modes of the first light source and the second light source between a normal mode in which the first light source and the second light source emit illumination light for illuminating a surrounding area and a treatment mode in which the first light source and the second light source emit treatment light for therapeutic use.

2. The treatment luminaire according to claim 1,
wherein the controller turns on the second light source in such a manner that the second light source emits brighter treatment light in the treatment mode than illumination light in the normal mode.

3. The treatment luminaire according to claim 1,
wherein the controller turns on the first light source in such a manner that the first light source emits darker treatment light in the treatment mode than illumination light in the normal mode.

4. The treatment luminaire according to claim 1,
wherein a ratio of blue light included in the treatment light emitted by the second light source in the treatment mode is larger than a ratio of blue light included in the illumination light emitted by the first light source in the normal mode or a ratio of blue light included in the illumination light emitted by the second light source in the normal mode.

5. The treatment luminaire according to claim 1,
wherein an amount of blue light included in the treatment light emitted by the second light source in the treatment mode is larger than an amount of blue light included in the illumination light emitted by the first light source in the normal mode or an amount of blue light included in the illumination light emitted by the second light source in the normal mode.

6. The treatment luminaire according to claim 1,
wherein when the controller causes the first light source and the second light source to operate in the treatment mode, the controller changes an output of light from at least one of the first light source and the second light source according to a crossing angle between the light distribution axis of the first light source and the light distribution axis of the second light source.

7. The treatment luminaire according to claim 1,
wherein the second light source comprises two second light sources, and the two second light sources are arranged on different sides of the first light source.

8. The treatment luminaire according to claim 7,
wherein when a light distribution axis of one of the two second light sources is tilted more than a threshold angle with respect to the light distribution axis of the first light source, the controller switches the operation modes of the first light source and the one of the two second light sources from the normal mode to the treatment mode.

9. The treatment luminaire according to claim 8,
wherein a ratio of blue light included in the treatment light emitted by the one of the two second light sources in the treatment mode is larger than a ratio of blue light included in the illumination light emitted by the first light source in the normal mode or a ratio of blue light included in the illumination light emitted by the one of the two second light sources in the normal mode.

10. The treatment luminaire according to claim 8,
wherein an amount of blue light included in the treatment light emitted by the one of the two second light sources in the treatment mode is larger than an amount of blue light included in the illumination light emitted by the first light source in the normal mode or an amount of blue light included in the illumination light emitted by the one of the two second light sources in the normal mode.

11. The treatment luminaire according to claim 7,
when a light distribution axis of one of the two second light sources is tilted more than a threshold angle with respect to the light distribution axis of the first light source, the controller changes outputs of light from the first light source and the one of the two second light sources according to a crossing angle between the light distribution axis of the first light source and the light distribution axis of the one of the two second light sources.

12. The treatment luminaire according to claim 1,
wherein when the controller causes the first light source and the second light source to operate in the treatment mode, the controller causes at least one of the first light source and the second light source to increase an output of light with an increase in the crossing angle between the light distribution axis of the first light source and the light distribution axis of the second light source.

13. The treatment luminaire according to claim 1,
wherein the treatment light is light including blue light having a peak wavelength in a range from 380 nm to 500 nm, and
the illumination light is a visible light having a peak wavelength in a range from 380 nm to 780 nm.

14. The treatment luminaire according to claim 1,
wherein the first light source emits light having a maximum luminance of 43000 $cd/m^2$ in the normal mode, and
when the light distribution axis of the second light source is tilted by 45 degrees with respect to the light distribution axis of the first light source, the second light source emits light having a maximum luminance of 75000 $cd/m^2$ in the treatment mode.

15. A treatment luminaire, comprising:
a first light source which selectively emits illumination light for illuminating a surrounding area and treatment light for therapeutic use;
a second light source which selectively emits illumination light for illuminating a surrounding area and treatment light for therapeutic use;
an adjuster for adjusting a crossing angle between a light distribution axis of the first light source and a light distribution axis of the second light source; and
a controller which switches, according to the crossing angle, operation modes of the first light source and the second light source between a normal mode in which the first light source and the second light source emit illumination light and a treatment mode in which the first light source and the second light source emit treatment light.

16. A mirror apparatus, comprising:
the treatment luminaire according to claim 7;
a first mirror on which the first light source is disposed; and
two second mirrors arranged on different sides of the first mirror, wherein the two second light sources are each disposed on a corresponding one of the second mirrors.

17. The mirror apparatus according to claim 16, wherein:
the adjuster is a hinge which connects the first mirror and a corresponding one of the two second mirrors,
the mirror apparatus further comprises an angle detector which detects a changing angle of the hinge as the crossing angle between the light distribution axis of the first light source and the light distribution axis of the second light source, and
the controller switches an operation mode of at least one of the first light source and a corresponding one of the second light sources between the normal mode and the treatment mode according to the changing angle of the hinge detected by the angle detector.

18. The mirror apparatus according to claim 17,
wherein the controller
switches the operation mode of the at least one of the first light source and the corresponding one of the second light sources from the normal mode to the treatment mode when the angle detector detects that the changing angle of the hinge reached or exceeded a predetermined angle, and
switches the operation mode of the at least one of the first light source and the corresponding one of the second light sources from the treatment mode to the normal mode when the angle detector detects that the changing angle of the hinge was reduced below the predetermined angle.

19. The mirror apparatus according to claim 16, further comprising:
a timer which measures time during which the first light source and the second light sources emit the treatment light,
wherein the controller emits the treatment light according to the time set by the timer.

20. The mirror apparatus according to claim 16,
wherein the first light source is disposed at an edge of the first mirror, and
each of the second light sources is disposed at an edge of a corresponding one of the second mirrors.

* * * * *